(12) United States Patent
Zdeblick et al.

(10) Patent No.: US 7,276,082 B2
(45) Date of Patent: Oct. 2, 2007

(54) ARTIFICIAL SPINAL DISCS AND ASSOCIATED IMPLANTATION AND REVISION METHODS

(75) Inventors: Thomas A. Zdeblick, Middleton, WI (US); Vincent C. Traynelis, Iowa City, IA (US); Regis W. Haid, Atlanta, GA (US); Greg C. Marik, Germantown, TN (US); Bradley J. Coats, Rossville, TN (US); Courtney S. Williams, Memphis, TN (US); Craig M. Squires, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 31 days.

(21) Appl. No.: 10/933,669

(22) Filed: Sep. 3, 2004

(65) Prior Publication Data
US 2005/0055098 A1   Mar. 10, 2005

Related U.S. Application Data

(60) Provisional application No. 60/501,929, filed on Sep. 10, 2003.

(51) Int. Cl.
*A61F 2/44*   (2006.01)
(52) U.S. Cl. .................. 623/17.15; 623/17.14; 623/17.11
(58) Field of Classification Search ......... 623/23.39, 623/17.15, 17.14, 20.22, 19.12, 23.4, 22.42, 623/22.16
See application file for complete search history.

(56) References Cited

U.S. PATENT DOCUMENTS

| 5,071,437 | A | | 12/1991 | Steffee |
| 5,258,031 | A | * | 11/1993 | Salib et al. ............... 623/17.15 |
| 5,425,773 | A | | 6/1995 | Boyd et al. |
| 5,534,029 | A | | 7/1996 | Shima |
| 5,562,738 | A | | 10/1996 | Boyd et al. |
| 5,782,832 | A | | 7/1998 | Larsen et al. |
| 5,824,094 | A | | 10/1998 | Serhan et al. |
| 5,888,227 | A | | 3/1999 | Cottle |
| 5,895,428 | A | | 4/1999 | Berry |
| 5,899,941 | A | | 5/1999 | Nishijima et al. |
| 5,989,291 | A | * | 11/1999 | Ralph et al. ............. 623/17.15 |
| 6,063,121 | A | * | 5/2000 | Xavier et al. ............ 623/17.15 |
| 6,096,080 | A | | 8/2000 | Nicholson et al. |
| 6,113,637 | A | * | 9/2000 | Gill et al. ................ 623/17.15 |
| 6,139,579 | A | | 10/2000 | Steffee et al. |
| 6,146,421 | A | * | 11/2000 | Gordon et al. ........... 623/17.15 |
| 6,162,252 | A | | 12/2000 | Kuras et al. |
| 6,228,118 | B1 | | 5/2001 | Gordon |
| 6,348,071 | B1 | | 2/2002 | Steffee et al. |

(Continued)

FOREIGN PATENT DOCUMENTS

WO   WO 2004/041131   5/2004

*Primary Examiner*—Alvin J. Stewart
(74) *Attorney, Agent, or Firm*—Haynes and Boone, LLP (57) ABSTRACT

An intervertebral device comprises a first endplate assembly including a first exterior surface, a second endplate assembly including a second exterior surface, and a bone in-growth area located on the first exterior surface. The bone in-growth area includes an osteoconductive surface. The intervertebral device also comprises a bone in-growth indicator located on the first exterior surface and an access guide on the first endplate. The access guide is adapted for directing a revision instrument to the bone in-growth area.

18 Claims, 12 Drawing Sheets

U.S. PATENT DOCUMENTS

| | | |
|---|---|---|
| 6,375,683 B1 * | 4/2002 | Crozet et al. ............ 623/17.15 |
| 6,454,806 B1 * | 9/2002 | Cohen et al. ............ 623/17.15 |
| 6,517,580 B1 | 2/2003 | Ramadan et al. |
| 6,520,993 B2 | 2/2003 | James et al. |
| 6,592,624 B1 * | 7/2003 | Fraser et al. ............ 623/17.16 |
| 6,616,695 B1 | 9/2003 | Crozet et al. |
| 6,641,614 B1 * | 11/2003 | Wagner et al. .......... 623/17.15 |
| 6,660,038 B2 | 12/2003 | Boyer et al. |
| 6,669,732 B2 | 12/2003 | Serhan et al. |
| 2001/0016773 A1 | 8/2001 | Serhan et al. |
| 2002/0022888 A1 | 2/2002 | Serhan et al. |
| 2002/0035400 A1 * | 3/2002 | Bryan et al. ............ 623/17.15 |
| 2002/0099443 A1 * | 7/2002 | Messerli et al. .......... 623/17.11 |
| 2003/0040802 A1 | 2/2003 | Errico et al. |
| 2003/0045940 A1 | 3/2003 | Eberlein et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0105527 A1 | 6/2003 | Bresina |
| 2003/0109928 A1 | 6/2003 | Pasquet et al. |
| 2003/0167091 A1 | 9/2003 | Scharf |
| 2003/0176922 A1 * | 9/2003 | Lawson et al. .......... 623/17.11 |
| 2003/0176925 A1 | 9/2003 | Paponneau |
| 2003/0181981 A1 | 9/2003 | Lemaire |
| 2003/0191533 A1 | 10/2003 | Dixon et al. |
| 2003/0191534 A1 | 10/2003 | Viart et al. |
| 2003/0204261 A1 | 10/2003 | Elsermann et al. |
| 2003/0208272 A1 | 11/2003 | Crozet et al. |
| 2003/0233145 A1 | 12/2003 | Landry et al. |
| 2003/0233146 A1 | 12/2003 | Grinberg et al. |
| 2003/0236526 A1 | 12/2003 | Van Hoeck et al. |
| 2003/0236571 A1 | 12/2003 | Ralph et al. |
| 2004/0002758 A1 | 1/2004 | Landry et al. |
| 2004/0010316 A1 | 1/2004 | William et al. |
| 2004/0133281 A1 * | 7/2004 | Khandkar et al. ....... 623/17.16 |
| 2004/0172021 A1 * | 9/2004 | Khalili ....................... 606/61 |
| 2004/0225362 A1 * | 11/2004 | Richelsoph ............... 623/17.13 |
| 2004/0225365 A1 * | 11/2004 | Eisermann et al. ...... 623/17.15 |
| 2004/0254644 A1 * | 12/2004 | Taylor ..................... 623/17.13 |
| 2005/0065611 A1 * | 3/2005 | Huppert et al. .......... 623/17.15 |
| 2005/0085917 A1 * | 4/2005 | Marnay et al. ........... 623/17.16 |
| 2005/0159819 A1 * | 7/2005 | McCormack et al. .... 623/17.16 |
| 2005/0228500 A1 * | 10/2005 | Kim et al. ................ 623/17.13 |
| 2006/0136061 A1 * | 6/2006 | Navarro et al. .......... 623/17.13 |
| 2006/0136062 A1 * | 6/2006 | DiNello et al. .......... 623/17.14 |
| 2006/0212123 A1 * | 9/2006 | Lechmann et al. ...... 623/17.15 |

* cited by examiner

ARTIFICIAL SPINAL DISCS AND ASSOCIATED IMPLANTATION AND REVISION METHODS

CROSS-REFERENCE

This application claims priority from U.S. Provisional Patent Application Ser. No. 60/501,929 filed on Sep. 10, 2003, and entitled "Artificial Spinal Discs And Associated Implementation Instruments And Methods." This application is also related to the U.S. patent application Ser. No. 10/894,557, titled "Artificial Spinal Discs And Associated Implementation Instruments And Methods."

BACKGROUND

The present invention relates to artificial spinal discs, and instruments and methods associated with the implantation of such artificial spinal discs.

Current spinal therapies for treating problematic spinal discs are moving from rigid fixation of adjacent vertebrae across the problematic disc space, such as with rods or plates, to maintaining the relative motion of the adjacent vertebrae, such as with artificial spinal discs. For instance, an artificial spinal disc may be utilized to treat degenerative disc disease, including a herniated nucleus pulposus and/or posterior osteophytes, which causes radiculopathy and/or myelopathy. Radiculopathy is compression of a spinal nerve root, while myelopathy is compression of the spinal cord. Both are conditions that may result in an individual experiencing pain or tingling in the arms, legs, back and/or neck.

Current artificial spinal discs have drawbacks relating to their fixation to the adjacent vertebrae and their ability to be revised, or removed, after their implantation. For instance, current artificial discs may have special contours that need to be machined into the endplates of the adjacent vertebrae. Further, current artificial discs may require special machining of the vertebrae and/or implantation instrumentation to accommodate spikes, fins, or other structures extending into the adjacent vertebrae that are used to fixate the disc to the vertebrae. Additionally, current artificial discs may include bone in-growth surfaces across the entire vertebrae-contacting surface. This makes it difficult to remove the artificial disc, as is sometimes required, once the artificial disc is implanted.

Similarly, the associated implantation instruments and methods have a number of drawbacks relating to their complexity or to their suitability for use in more sensitive areas of the spine, such as in the cervical spine. For instance, some implantation systems require the use of many different instruments and devices to prepare the disc space and properly insert the artificial disc. Further, some implantation systems rely on impacting, or hammering, features into the bone to accommodate the artificial disc. Such impaction techniques may be suitable in certain areas of the spine, like in the lumbar spine, but are not as desirable in other areas of the spine, like the cervical spine, where the proximity of the spinal cord and nerve roots would favor more delicate procedures.

SUMMARY

In one embodiment, an intervertebral device comprises a first endplate assembly including a first exterior surface, a second endplate assembly including a second exterior surface, and a bone in-growth area located on the first exterior surface. The bone in-growth area includes an osteoconductive surface. The intervertebral device also comprises a bone in-growth indicator located on the first exterior surface and an access guide on the first endplate. The access guide is adapted for directing a revision instrument to the bone in-growth area.

In another embodiment, a method of removing an intervertebral prosthesis from between first and second vertebral bodies comprises the step of identifying a predefined osteoconductive area on an endplate assembly of the intervertebral prosthesis. The osteoconductive area is affixed to the first vertebral body by in-grown bone. The method further comprises the step of identifying an access guide on the endplate assembly adjacent to the osteoconductive area and inserting a revision instrument between the first vertebral body and the endplate assembly along the access guide. The method also includes the step of separating the endplate assembly from the first vertebral body.

BRIEF DESCRIPTION OF THE DRAWINGS

The various embodiments of the present invention will hereinafter be described in conjunction with the appended drawings provided to illustrate and not to limit the present invention, wherein like designations denote like elements, and in which.

DETAILED DESCRIPTION

The present invention relates to artificial disc systems, and methods and devices associated with implanting these disc systems into a spine. The artificial disc systems provide predetermined bone in-growth areas that allow for revising or removing the artificial disc after implantation and bony in-growth. Further, the artificial disc systems include structural features that improve instrument accessibility in performing such a revision. Additionally, the artificial disc systems include structures for stabilizing the disc within the associated vertebrae. And, the associated instruments and devices simplify the implantation of the artificial disc systems, as well as providing less traumatic insertion of the systems into the disc space.

Figure 1:
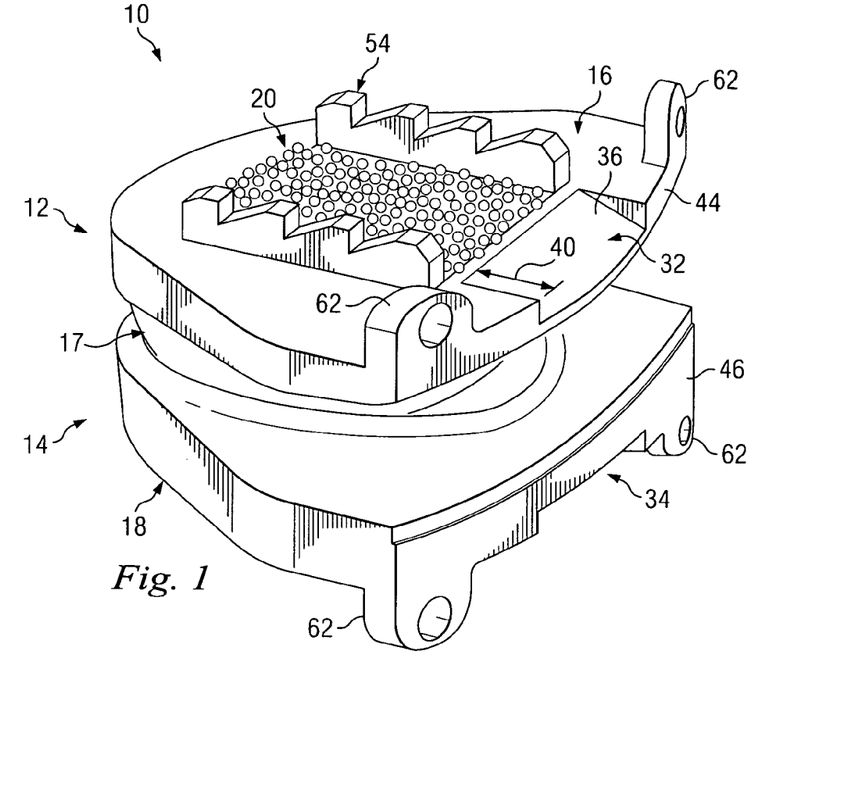
FIG. 1 is a perspective view of an artificial spinal disc system.
Figure 2:
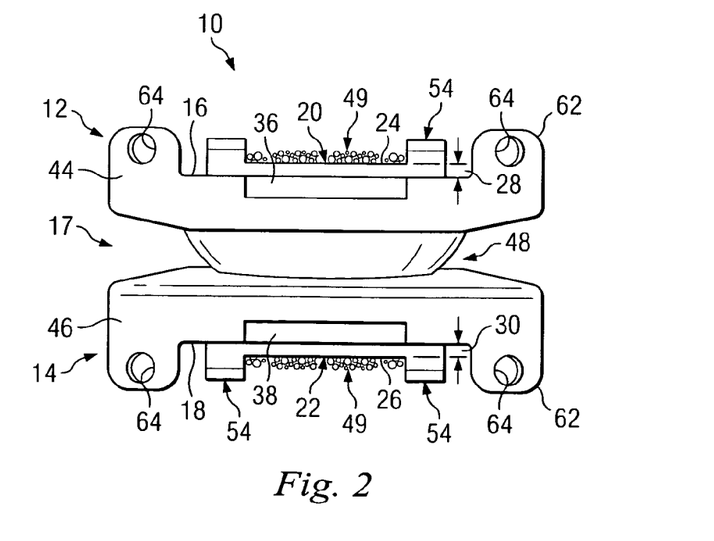
FIG. 2 is a front view of the artificial spinal disc system of FIG. 1.
Figure 3:
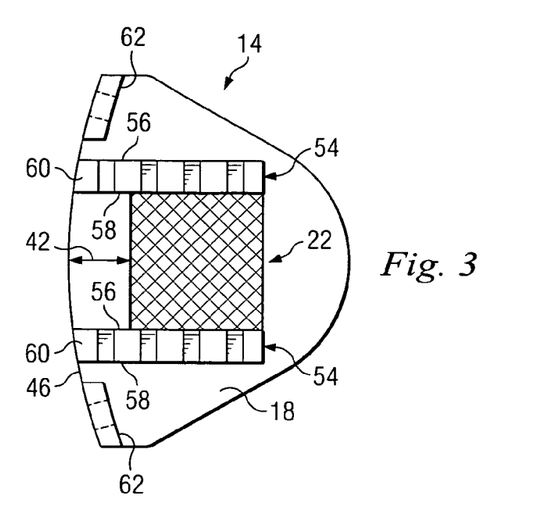
FIG. 3 is a bottom view of a second or inferior member of the artificial disc system of FIG. 1.
Figure 4:
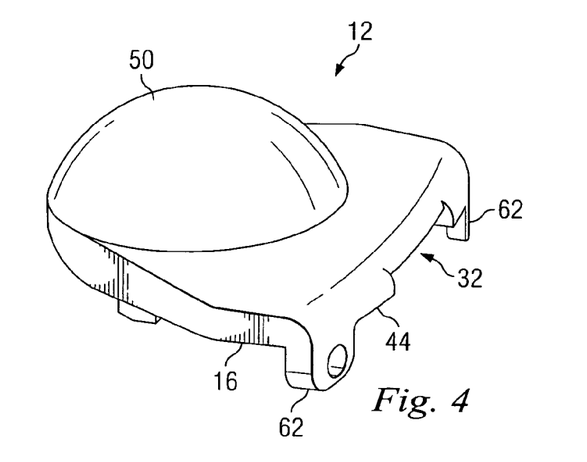
FIG. 4 is a perspective view of an inner surface of a first or superior member of the artificial disc system of FIG. 1.
Figure 5:
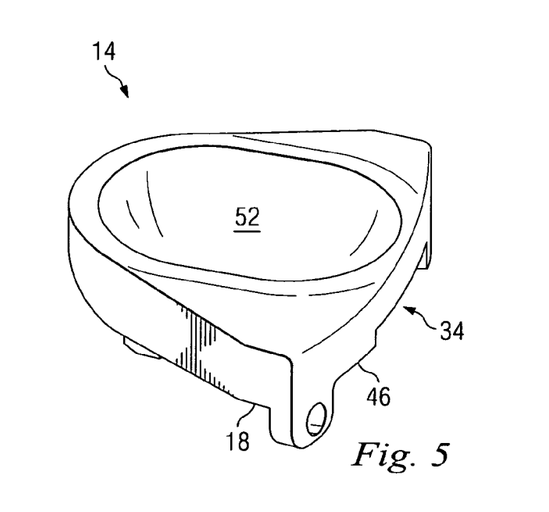
FIG. 5 is a perspective view of an inner surface of a second or inferior member of the artificial disc system of FIG. 1.
Figure 6:
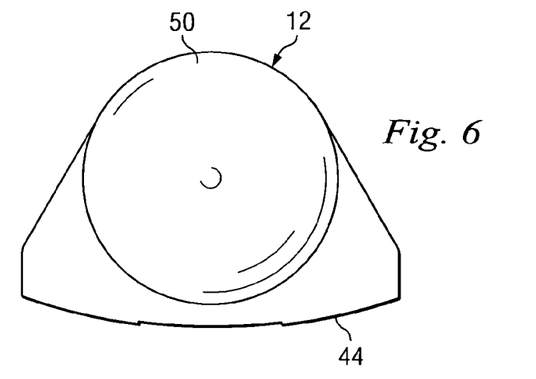
FIG. 6 is a bottom or inferior view of an inner surface of a first or superior member of the artificial disc system of FIG. 1.
Figure 7:
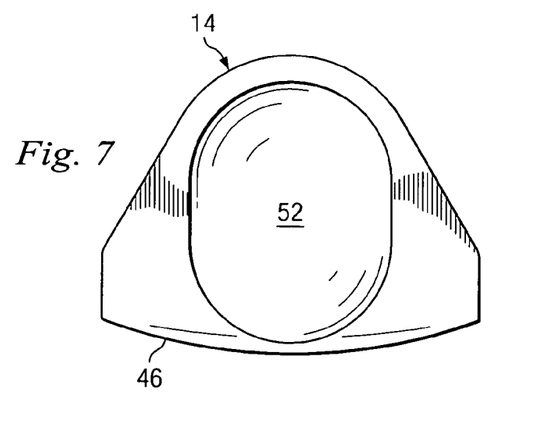
FIG. 7 is a bottom or inferior view of an inner surface of a second or inferior member of the artificial disc system of FIG. 1.

Referring to FIGS. 1-3, one embodiment of an artificial spinal disc system 10 includes a first member 12 movable relative to a second member 14 via an articulation component 17. Each of first and second members 12, 14 include at least one bone-contacting surface 16, 18 for placement against a portion of an adjacent vertebral bone. Each bone-contacting surface 16, 18 may include at least one bone in-growth surface 20, 22 of a predetermined size and shape, and in a predetermined position and orientation on the respective surface 16, 18. The predetermined size, shape, positioning and orientation of bone in-growth surface 20, 22 allows for a calculated amount of bone growth into the disc members 12, 14 for secure fixation to the adjacent bone, while allowing for easy removal of the disc member from the adjacent bone after bone in-growth occurs if such removal is required at a later date by changing medical needs. Further, the top surface 24, 26 of bone in-growth surface 20, 22 may have a predetermined spacing 28, 30 (FIG. 2) above the remaining portion of bone-contacting surface 16, 18 to allow for increased penetration and/or compression of the adjacent vertebral bone into bone in-growth surface 20, 22 upon implantation of artificial disc system 10. Additionally, each member 12, 14 may include at least one bone in-growth area indicator 32, 34 that identifies the location of the bone in-growth surface 20, 22. For instance, after artificial disc system 10 is implanted, bone in-growth area indicator 32, 34 provides a visual marker that can be seen by the naked eye, such as through an incision that exposes a surface of the system 10, or by medical diagnostic equipment, such as x-ray, ultrasound, magnetic resonance, computed tomography, positron emission technology, and other such diagnostic techniques. Further, bone in-growth area indicator 32, 34 may further include an instrument access guide 36, 38 that cooperates with a medical instrument, such as an osteotome, used in removing artificial disc system 10. Instrument access guide 36, 38 directs the instrument to the exact position of bone in-growth surface 20, 22, thereby avoiding unnecessary work in non-bone-in-growth areas of bone-contacting surface 16, 18 and without interfering with other structures that may be present on surfaces 16, 18. Thus, artificial disc system 10 provides features for secure fixation to adjacent vertebral bone while allowing for easy removal of all or a portion of the system if later required by changing medical needs.

Bone in-growth surface 20, 22 generally has a size that is substantially less than the overall size of the respective bone-contacting surface 16, 18. Further, bone in-growth surface 20, 22 may be positioned on respective bone-contacting surface 16, 18 such that after implantation bone in-growth surface 20, 22 is located proximal to cancellous bone portions, rather than cortical bone portions, of the adjacent vertebral bone. Such positioning, for example, may be at the center of member 12, 14 for a disc system that substantially spans the disc space or vertebral endplate. Alternatively, such positioning may be off-center with respect to member 12, 14 if the disc system only spans a portion of the disc space or vertebral end plate. Additionally, bone in-growth surface 20, 22 may be positioned at a predetermined spacing 40, 42 from an edge 44, 46 of member 12, 14 that is exposed after implantation of the system 10, such as an edge that is not within the disc space between the adjacent vertebrae. Predetermined spacing 40, 42 allows for easier entry of an instrument, such as an osteotome, that is used to separate member 12, 14 from the vertebral bone after bony in-growth has occurred. Furthermore, bone in-growth surface 20, 22 may lie in a single plane, or may lie in one or more planes, which may be intersecting planes, if more secure fixation and bony in-growth is desired. Suitable examples of bone in-growth surface 20, 22 may include surfaces that are chemically-etched, machined, sprayed, layered, fused, coated or textured in any manner or with any material that allows for the growth and attachment of bone.

Bone in-growth indicator 32, 34 may include any type of marker, such as an indentation, an embedded marker, coatings, projections, etc., on any surface of member 12, 14. Further, instrument access guide 36, 38 may include any surface or combination of surfaces that work in cooperation with a surface or portion of a medical instrument used from separating member 12, 14 from bone. Alternatively, instrument access guide 36, 38 may comprise a marker to indicate a position in computer- and/or image-guided surgery.

Further, referring to FIG. 2, securing of the artificial disc system 10 to bone may be enhanced by applying a bone growth promoting substance 49 to a bone contacting surface 16, 18 of the artificial disc system. In particular, bone growth promoting substance 49 may be applied to one or more bone in-growth surfaces 22 to encourage bone to growth into this area. Suitable examples of bone growth promoting substances include bone morphogenic protein ("BMP"), LIM mineralization protein ("LMP"), demineralized bone matrix ("DBM"), mesenchymal stem cells, blood platelet gel, and other similar materials.

Articulation component 17 may be a structure integral with, or separable from, one or both of first member 12 and the second member 14. Referring to FIGS. 4-7, for example, in one embodiment articulation component 17 includes a joint 48 defined by at least a partly convex or curvilinear surface 50, such as a substantially spherical ball, projecting from first member 12 movable in at least a partly concave or curvilinear surface 52, such as an elongated socket, formed within second member 14. Alternatively, articulation component 17 may be an entirely separate member or combination of members, such as a ball, disc, nucleus, flexible and/or elastic component, etc., positionable in combination with first and second members 12, 14 to allow relative rotational and/or translational motion between the first and second members. Furthermore, first and second member 12, 14 and articulation member 17 may be interconnected to form a single assembly.

Additionally, artificial disc system 10 may include at least one fin or rail member 54 projecting out of bone contacting surface 16, 18 on at least one of first or second member 12, 14. Fin or rail member 54 provides surfaces 56, 58 positioned substantially normal to bone contacting surface 16, 18 that oppose translational or rotational movement of member 12, 14 within adjacent vertebral bone in a plane parallel to the surfaces 16, 18. It should be noted, however, that the particular orientation of surfaces 56, 58 may be adjusted to resist relative motion in any desired plane or direction. Additionally, fin or rail member 54 may include a top engagement surface 60, such as may be formed by teeth, knurling, texturing, etc., that further resists movement of member 12, 14 within bone. For example, for an artificial spinal disc system 10 inserted into the disc space from the anterior side, top engagement surface 60 may resist movement of the implanted disc in the anterior direction by allowing bone to grow or be positioned in the medial lateral direction between portions of the top engagement surface. Surface 60 may be oriented to resist relative motion between member 12, 14 and bone in a different direction, but in the same plane, as surfaces 56, 58. It should be noted, however, that surfaces 56, 58 and 60 may be oriented in a manner to resist any combination of directions of relative motion. Additionally, top engagement surface 60, as well as surface 56, 58 may be formed with angled or other biased surfaces that have a greater resistance to motion in one or more desired directions. For example, top engagement surface 60 may include a plurality of teeth defined by at least two surfaces, where at least one surface is substantially normal to bone contacting surface 16, 18 and the other wall is substantially non-orthogonally-angled relative to bone contacting surface 16, 18.

Further fin or rail member 54 may lie along a line oriented parallel to an insertion direction, where the insertion direction is a direction in which artificial spinal disc system 10, or either individual member 12, 14, is inserted into position between adjacent vertebrae. It should be understood, however, that fin or rail member 54 may lie along a curvilinear line, and may be angled with respect to the insertion direction. Additionally, fin or rail member 54 may be of any predetermined length. For example, fin or rail member 54 may be of a length greater than or less than the overall edge-to-edge length of artificial spinal disc system 10. For instance, fin or rail member 54 may be of a length such that it is spaced apart from any edge of the disc system 10, or one or both ends of the fin or rail member may be substantially parallel with an edge of the disc system. When an end of fin or rail member 54 is parallel with an edge of disc system 10, such as exposed edge 44, 46, then the fin or rail member may act as bone in-growth indicator 32, 34 and/or instrument access guide 36, 38.

Additionally, artificial spinal disc system 10 may include tabs 62 or other longitudinally extending members that allow the disc system to be held with an insertion instrument. For instance, tabs 62 may include one or more connector structures 64 (FIG. 2), such as an internal wall that defines a cavity or hole, that correspond with engaging features on an insertion instrument that is utilized to hold and/or insert one or both members 12, 14. Alternatively, connector structure 64 may include projections that extend into corresponding holes or cavities in the insertion instrument. Further, tabs or extending members 62 may prevent movement of member 12, 14 relative to the overlapping bone after implantation. For example, for a disc system 10 that is inserted between adjacent vertebrae from the anterior side, tabs or extending members 62 project away from the disc space and over the anterior portion of the vertebral body, thereby preventing relative movement of the member 12, 14 in the posterior direction.

First member 12, second member 14 and articulation component 17 each may be formed from any combination of one or more different biocompatible materials. Suitable materials include stainless steel, cobalt chrome, titanium, rubber, elastomer, polymers, etc., including all alloys and variations of these materials.

Figure 8:
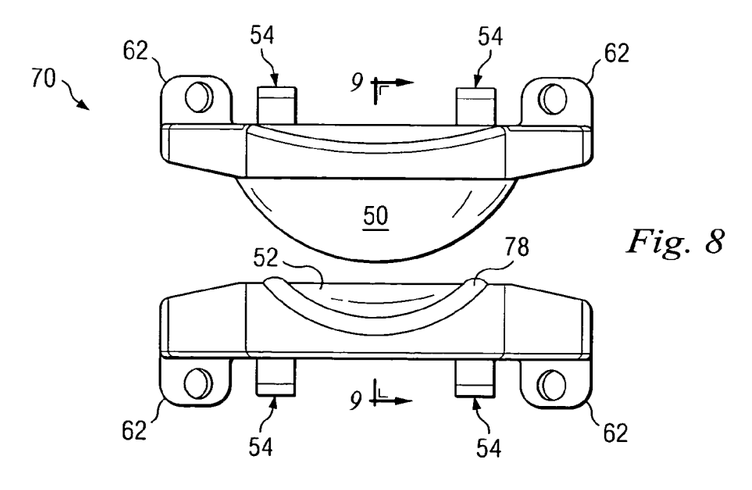
FIG. 8 is a rear view of another artificial spinal disc system.
Figure 9:
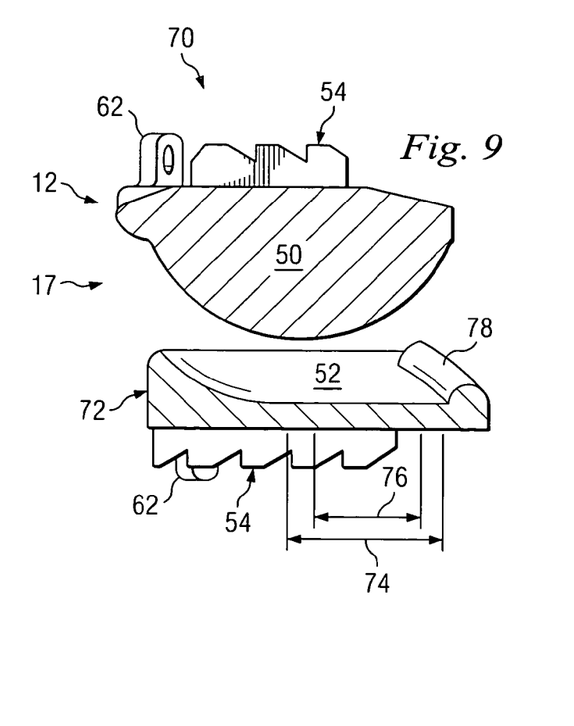
FIG. 9 is a cross-sectional view along line 9-9 of the artificial disc system of FIG. 8.

Referring to FIGS. 8 and 9, in another embodiment, artificial spinal disc system 70 may include a first member 12 movable relative to a second member 72, where such movement has a predetermined range of motion 74, in at least one direction, greater than the natural range of motion 76 of the natural disc being replaced. For instance, in an embodiment where articulation component 17 comprises a convex surface 50 interacting with a concave surface 52, the concave surface 52 may have a predetermined range of motion 74 corresponding to an anterior-to-posterior translation greater than that of the natural range of anterior-to-posterior translation of the natural disc being replaced. For example, for a spinal disc anterior-to-posterior translation typically corresponds to flexion and extension movements of the spinal motion segment, which movements would typically be constrained by natural tissue, including muscle, tendons, annulus fibrosus and/or facet joints. Thus, it may not be necessary to provide physical constraints within disc system 70 that limit the movement of first member 12 and second member 72, and hence articulation component 17, as the natural structure of the tissue adjacent the implanted artificial spinal disc system 70 may naturally limit the relative motion of the disc system. It should be noted that the predetermined range of motion 74 may be in any combination of one or more directions or planes, and may complete overlap the natural range of motion 76, be biased toward one side of the natural range of motion, or be within one side but extend beyond the other side of the natural range of motion. Additionally, although not required, artificial spinal disc system 70 may include a safety stop 78 positioned outside of the natural range of motion 76 to ultimately limit the movement of first member 12 relative to second member 72. Safety stop 78 may be formed in first member 12, second member 72 or in articulation component 17.

Figure 10:
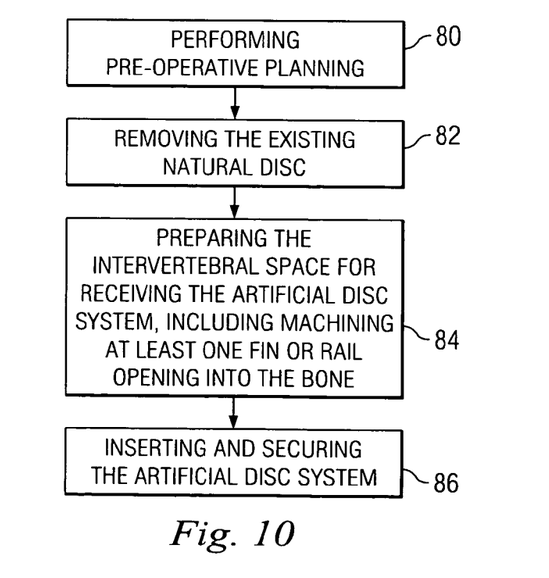
FIG. 10 is a flowchart of a method of implanting an artificial spinal disc system.

Referring to FIG. 10, embodiments of a method of implanting an artificial spinal disc system includes performing pre-operative planning (Block 80), removing the existing natural disc (Block 82), preparing the intervertebral space for receiving the artificial disc system (Block 84), and inserting and securing the artificial disc system (Block 86). The action of pre-operative planning may include examining the patient, taking x-rays or performing other diagnostic procedures to analyze the natural disc at issue, analyzing and/or calculating the existing or natural range of motion of the spinal motion segment, and/or measuring the natural disc space at issue to determine an appropriate size artificial disc system. The action of removing the natural disc may include a procedure such as a discectomy or partial discectomy, or any other procedure that removes all or a portion of the natural disc nucleus pulposus. The action of preparing the intervertebral space for receiving the artificial disc system may include contouring the end plates of the adjacent vertebrae. Such contouring may include forming parallel surfaces, forming concave surfaces, or forming any other shape in the end plate to receive the artificial disc system. In particular, as will be discussed in more detail below, the action of contouring the end plates may further include machining at least one fin or rail opening to receive a corresponding at least one fin or rail member associated with the artificial disc system. The action of machining may include removing a channel of bone from the end plate using tool having a surface adapted for removing bone, where the tool is capable of rotating, vibrating, reciprocating or otherwise acting on the end plate to remove bone. Further, the action of inserting and securing the artificial disc system may include holding a single component or the entire assembled artificial disc system and moving it into the prepared intervertebral disc space until it reaches a predetermined desired position. Securing the artificial disc system may occur naturally due to the compressive forces acting across the implanted artificial disc system, or may occur due to the contouring of the end plates, or may occur due to supplemental fixation techniques such as applying a screw or other separate component to hold a component of the system to the vertebral bone, or may occur as some combination of these techniques. Further, securing of the artificial disc system may be further achieved by applying a bone growth promoting substance to a bone contacting surface of the artificial disc system. Suitable examples of bone growth promoting substances include bone morphogenic protein ("BMP"), LIM mineralization protein ("LMP"), demineralized bone matrix ("DBM"), mesenchymal stem cells, blood platelet gel, and other similar materials. It should be noted that the above method may be achieved through an open surgical site, or in a minimally invasive manner such as through a tube or channel that allows from a relatively small opening in the skin and tissue of the patient compared to the open procedure.

Figure 11:
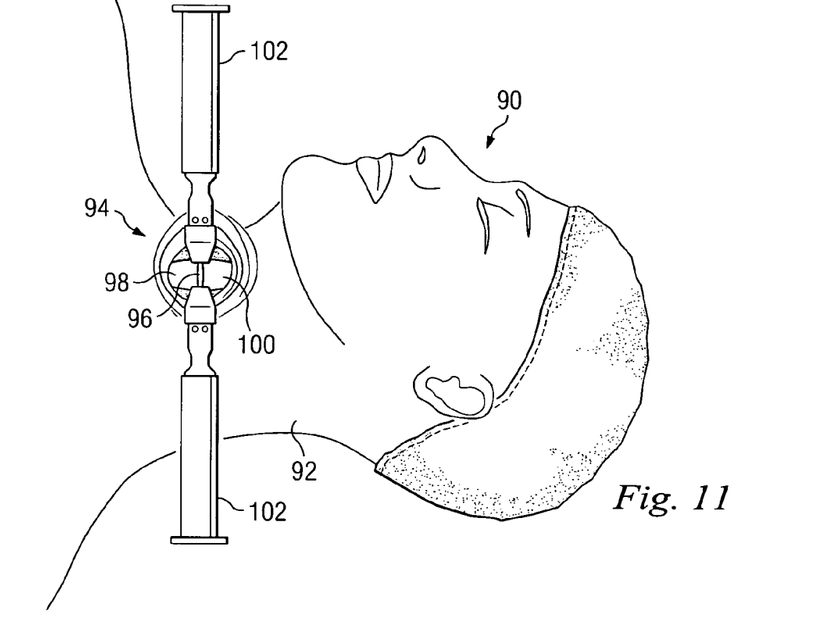
FIG. 11 is a representation of a patient positioned for spinal surgery, including a method of forming an access channel to access the natural spinal disc and the adjacent vertebral bodies.
Figure 12:
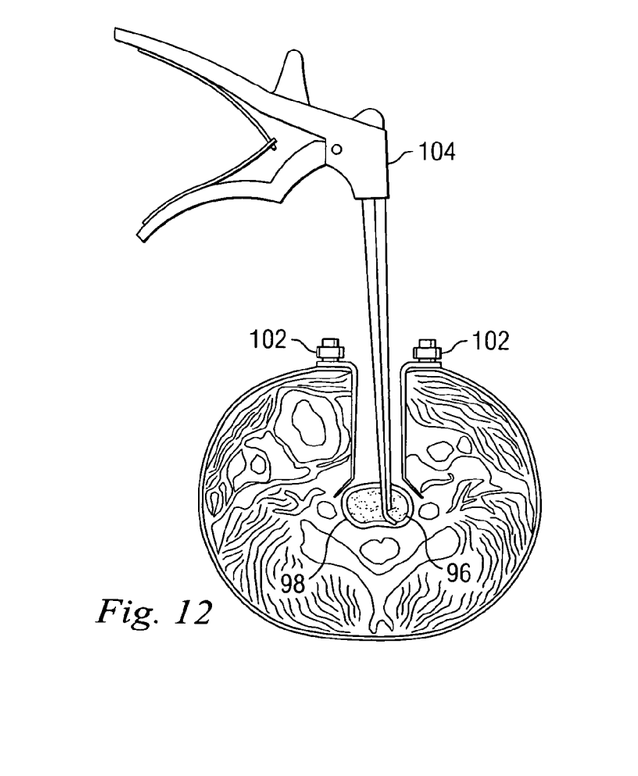
FIG. 12 is a representation of a method of removing the natural spinal disc of FIG. 11.

Referring to FIGS. 11-26, an embodiment of a method of implanting an artificial spinal disc system in the cervical portion of the spine includes positioning the patient for surgery, performing a discectomy and decompressing the disc space, preparing the adjacent vertebral endplates, and inserting the artificial spinal disc. Referring to FIG. 11, the patient 90 may be positioned such that their neck 92 is in a neutral position corresponding to the natural lordosis of the cervical spine. After making an incision, an access channel 94 to the natural spinal disc 96 and/or adjacent vertebrae 98, 100 may be maintained by an opener mechanism 102, such as one or more retractor blades or an endoscopic port or channel, respective examples including a TRIMLINE retractor blade or an X-TUBE endoscopic port both manufactured by Medtronic Sofamor Danek USA (Memphis, Tenn.). Then, referring to FIG. 12, the natural spinal disc 96 is removed using a disc removal instrument 104, such as a curette, osteotome or any instrument specifically designed for removal of all or a portion of the natural disc. After removal of all or a portion of the natural spinal disc 96, the disc space is decompressed, such as by using the Smith-Robinson decompression technique.

Figure 13:
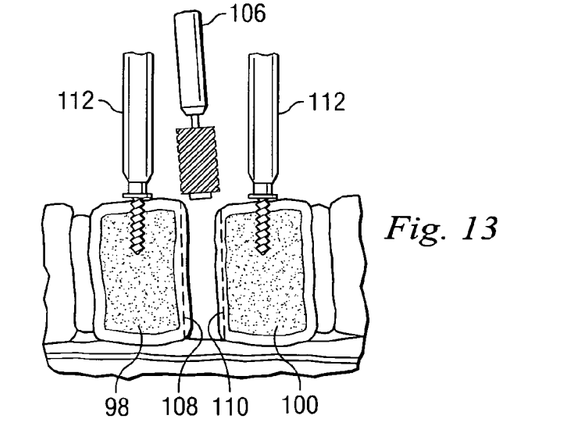
FIGS. 13-14 are representations of a method of forming a predetermined contour in one or both end plates of adjacent vertebral bodies of FIG. 11.
Figure 14:
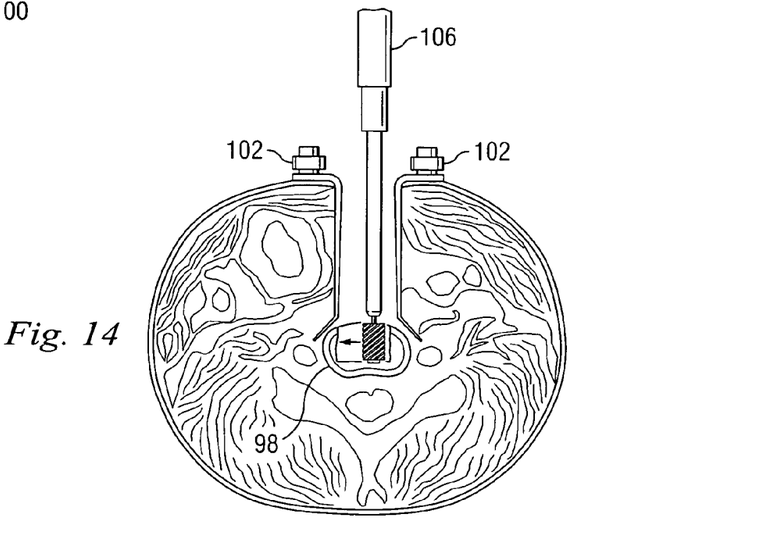
Figure 15:
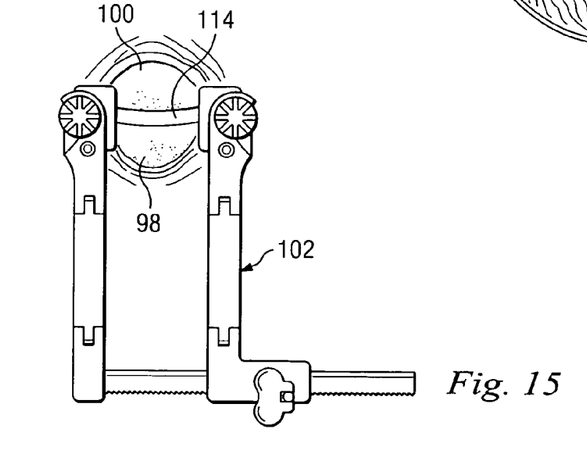
FIG. 15 is a representation of a prepared disc space following the procedure of FIGS. 13-14.

Referring to FIGS. 13-15, after removal of the natural disc, referred to as a discectomy, and decompression, at least one contouring device 106 may be utilized to form a predetermined contour 108, 110 which may generally correspond to the bone contacting surface of the artificial disc, into one of both of the adjacent vertebral bodies 98, 100. For example, in one embodiment, the vertebral end plates are machined to be flat and parallel, such as by using a cylindrical burr. It should be noted, however, that other contouring devices 106, such as mills, cutters, saws, etc., and other predetermined shape-forming devices may be used to remove bone from the end plates. In order to avoid subsidence of the artificial disc system into the end plates, the machining process may be performed to preserve as much cortical bone as possible. Additionally, referring specifically to FIG. 13, it should be noted that a reference device 112, such as a frame or such as markers, may be used in conjunction with contouring device 106 to control or guide the movements of the contouring device. For instance, reference device 112 may be attached to one or both adjacent vertebrae 98, 100 so as to provide geometric guidance to contouring device 106. After end plate contouring is complete, then the prepared disc space 114 (FIG. 15) may be ready for disc insertion and all external distraction may be removed.

Figure 16:
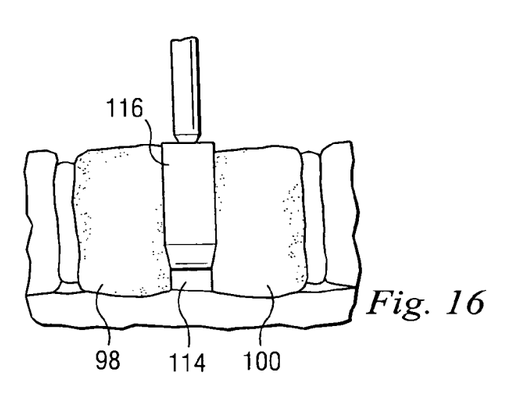
FIG. 16 is a representation of determining a size of the prepared disc space of FIG. 15.
Figure 17:
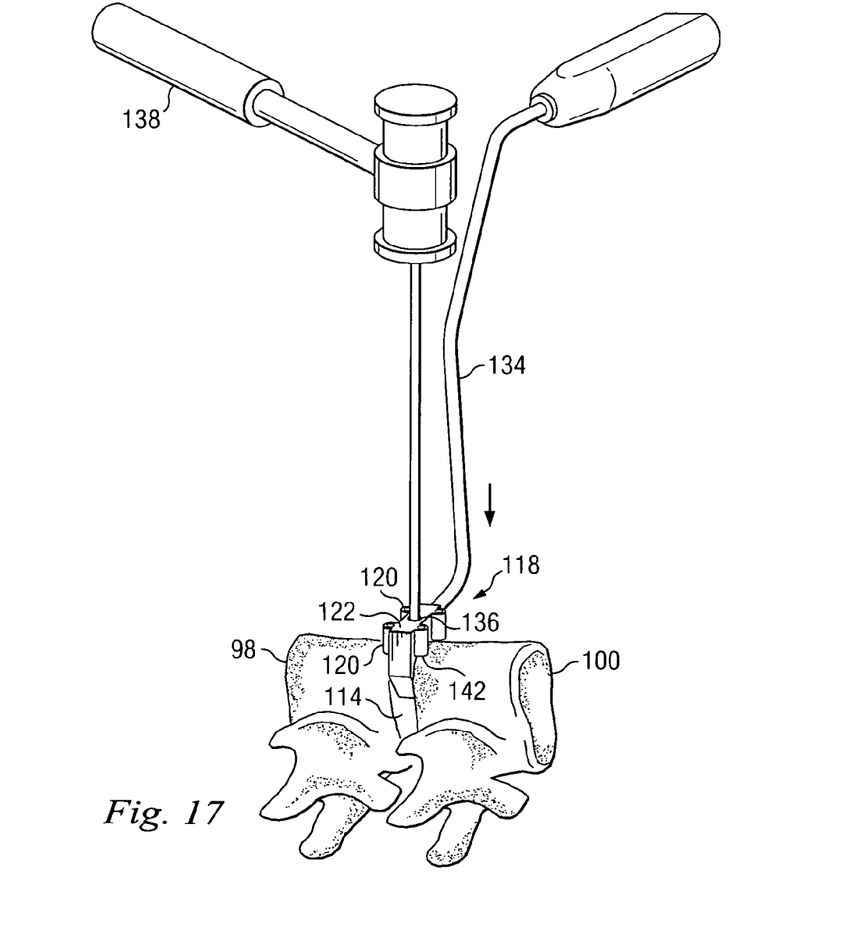
FIGS. 17-18 are representations of a rail cutter guide and method for forming one or more fin or rail guide channels in one or both end plates adjacent to the prepared disc space of FIG. 15.
Figures 18, 19:
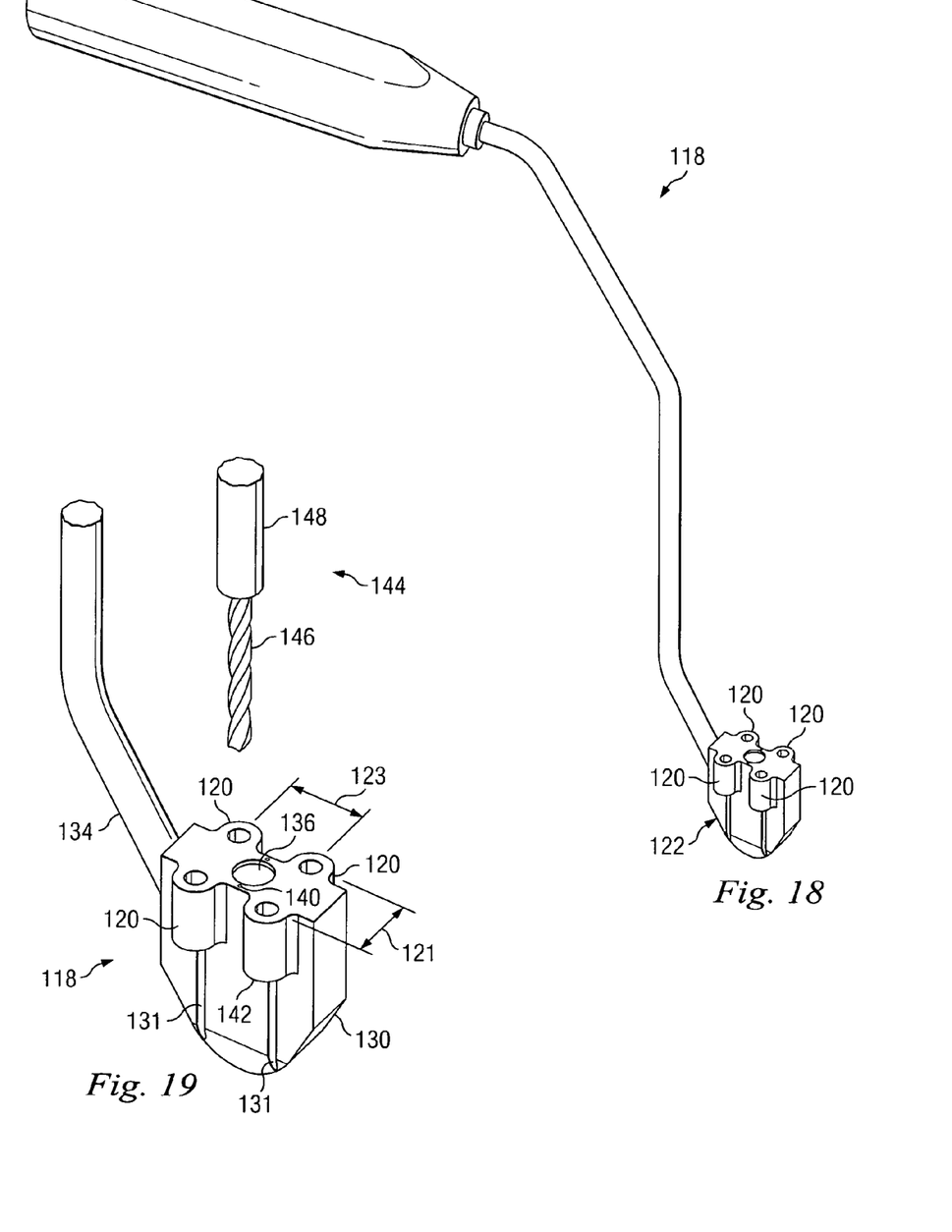
FIGS. 19-20 are representations of a bone removal mechanism being utilized in conjunction with the rail cutter guide of FIGS. 17-18.

Referring to FIG. 16, in order to determine the proper size artificial disc to use, an implant trial 116 may be inserted determine the size of the prepared disc space 114. In some embodiments that desire to avoid excessive compressive forces on the artificial disc system, the properly sized implant trial 116 fits snug in the prepared disc space 114 but does not distract the adjacent vertebrae 98, 100. Additionally, the fit of implant trial 116 may be confirmed diagnostically, such as with fluoroscopy. Referring to FIG. 17, once the appropriate sized implant trial 116 is determined, the correspondingly sized rail cutter guide 118 is selected and used to prepare one or more fin or rail channels in the endplates in correspondence with the fin or rail member on the artificial disc system.

Referring to FIGS. 17-22, one embodiment of a rail cutter guide 118 includes at least one machining guide 120 positioned on guide body 122 and having a size 124 to provide a reference to a bone cutting device 126 to form a fin or rail member channel 128 in one or both adjacent vertebrae 98, 100 corresponding in position and size to the fin or rail guide member on the artificial spinal disc system. In embodiments having more than one machining guide 120, referring specifically to FIG. 19, each machining guide 120 may have a predetermined longitudinal spacing 121 and/or a predetermined lateral spacing 123 with respect one or more of the other machining guides. Such predetermined spacing 121, 123 is advantageous for insuring formation of at least two fin or rail member channels 128 (FIG. 22), either in one vertebral end plate or in adjacent end plates, that are in alignment with the predetermined spacing of at least two or more fin or rail members on an artificial spinal disc selected to be implanted. Further, rail cutter guide 118 may include a spacer portion 130 sized and having a thickness 132 (FIG. 20) corresponding to a desired disc spacing, such as the natural neutral disc spacing of the prepared disc space 114. Additionally, guide body 122 or spacer portion 130 may include predetermined recesses 131 sized to accommodate at least a portion of a bone removal device. Rail cutter guide 118 may further include a permanent or removably attachable handle 134 for manipulating the position of the guide. Referring specifically to FIG. 17, rail cutter guide 118 may further include an engagement structure 136, such as a protrusion or an extension, that interacts with urging mechanism 138, such as a hammer-like or moving-weight type device, for moving the guide 118 into proper position. Rather than, or in addition to, being referenced to the prepared disc space 114 and/or the adjacent vertebrae 98, 100 via spacer portion 130, rail cutter guide 118 may include one or more reference markers 140 so as to insure a desired positioning with respect to the adjacent vertebrae. The desired positioning, for example, may include a cephalad-caudal positioning, a lateral positioning, a depth within the prepared disc space 114 positioning, and any combination thereof. For example, reference marker 140 may include a limiting structure 142 projecting from guide body 122 so as to limit the depth of penetration of the guide body into prepared disc space 114. Further, one or more reference markers 140 may be associated with any other structure having a known position relative to one or both vertebrae 98, 100 and/or prepared disc space 114.

Figures 20, 21:
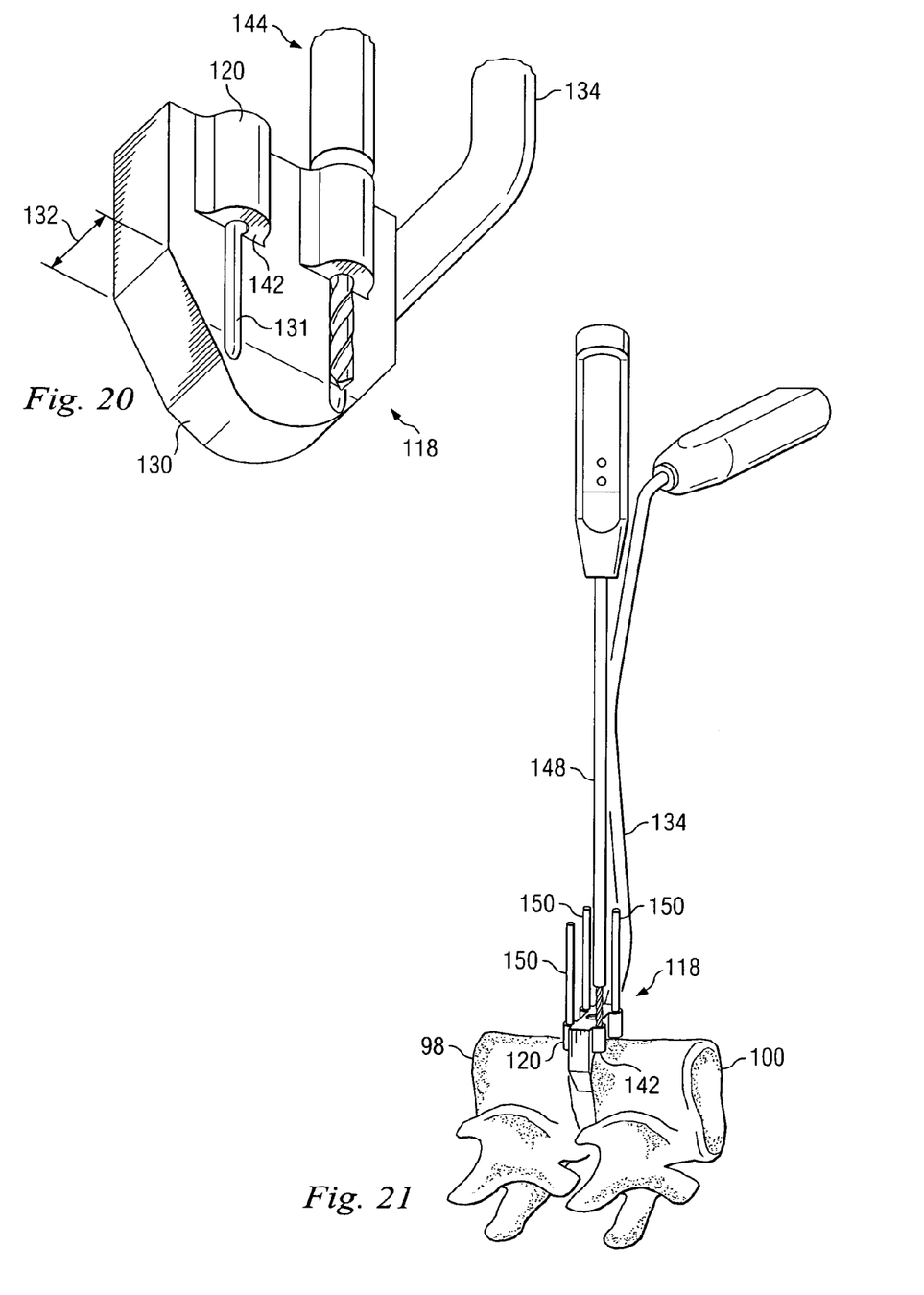
FIG. 21 is a representation of a temporary fixation of the rail cutter guide with respect to one or more adjacent vertebrae using temporary fixation members.
Figure 22:
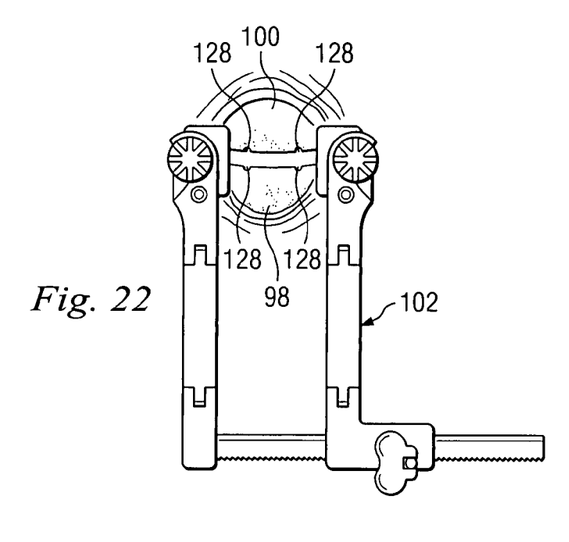
FIG. 22 is a representation of the prepared disc space of FIG. 15 with the addition of fin or rail guide channels formed via the methods of FIGS. 17-21.
Figure 23:
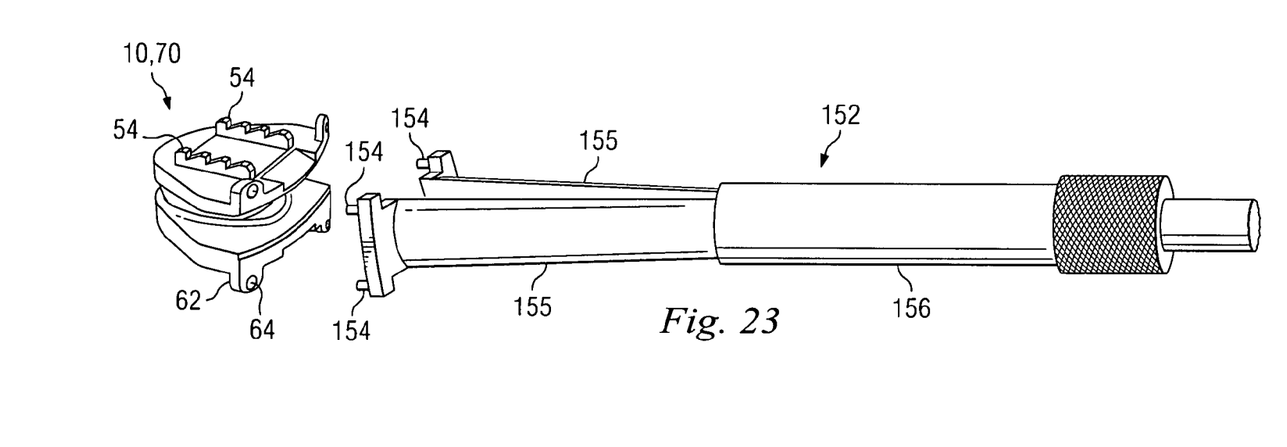
FIG. 23 is a perspective view of an artificial spinal disc system and an implant inserter for holding and inserting the disc system into the disc space of FIG. 22.
Figure 24:
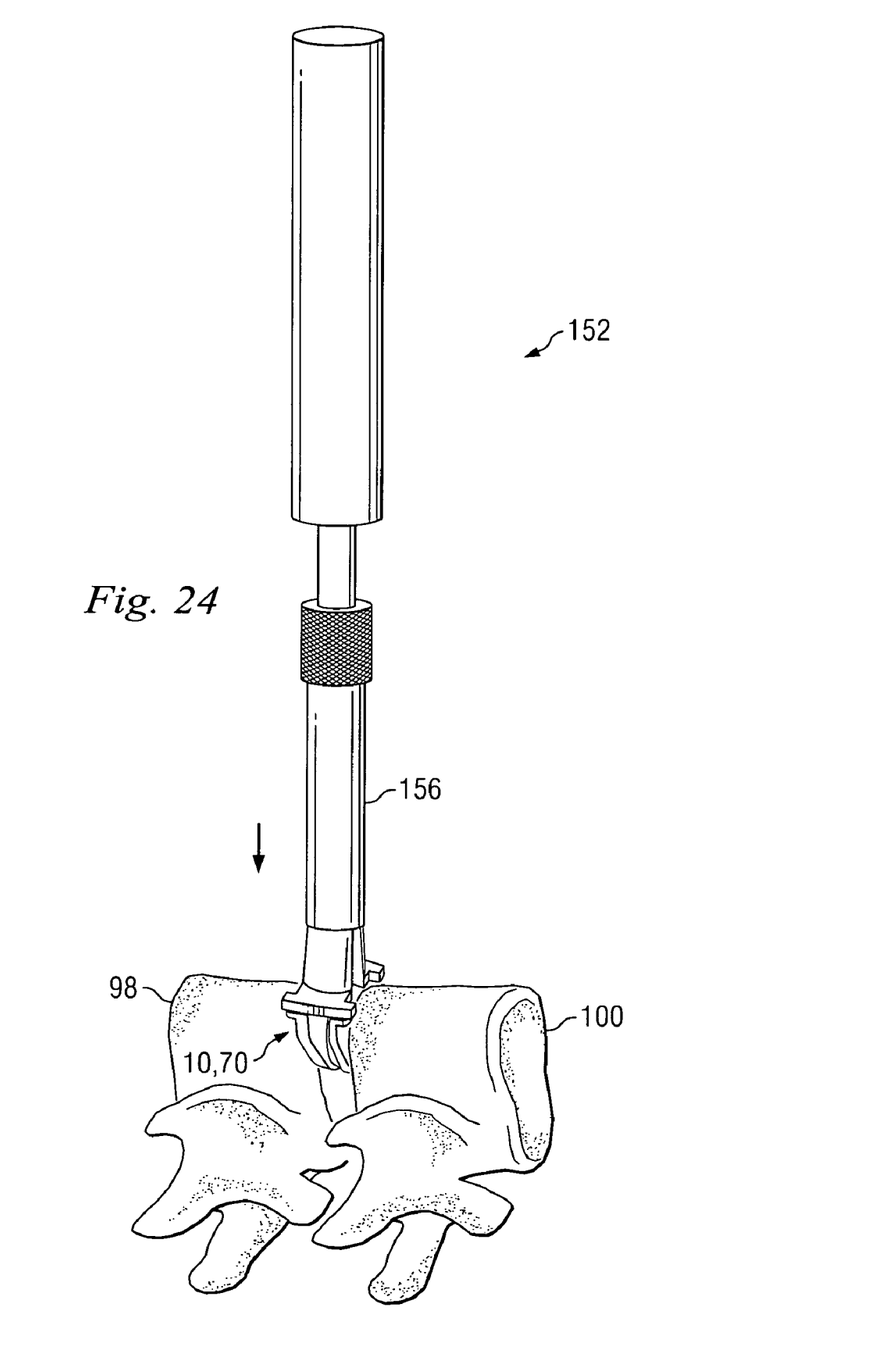
FIG. 24 is a perspective view of a representation of a method of inserting an artificial spinal disc system into the disc space of FIG. 22.
Figures 25, 26:
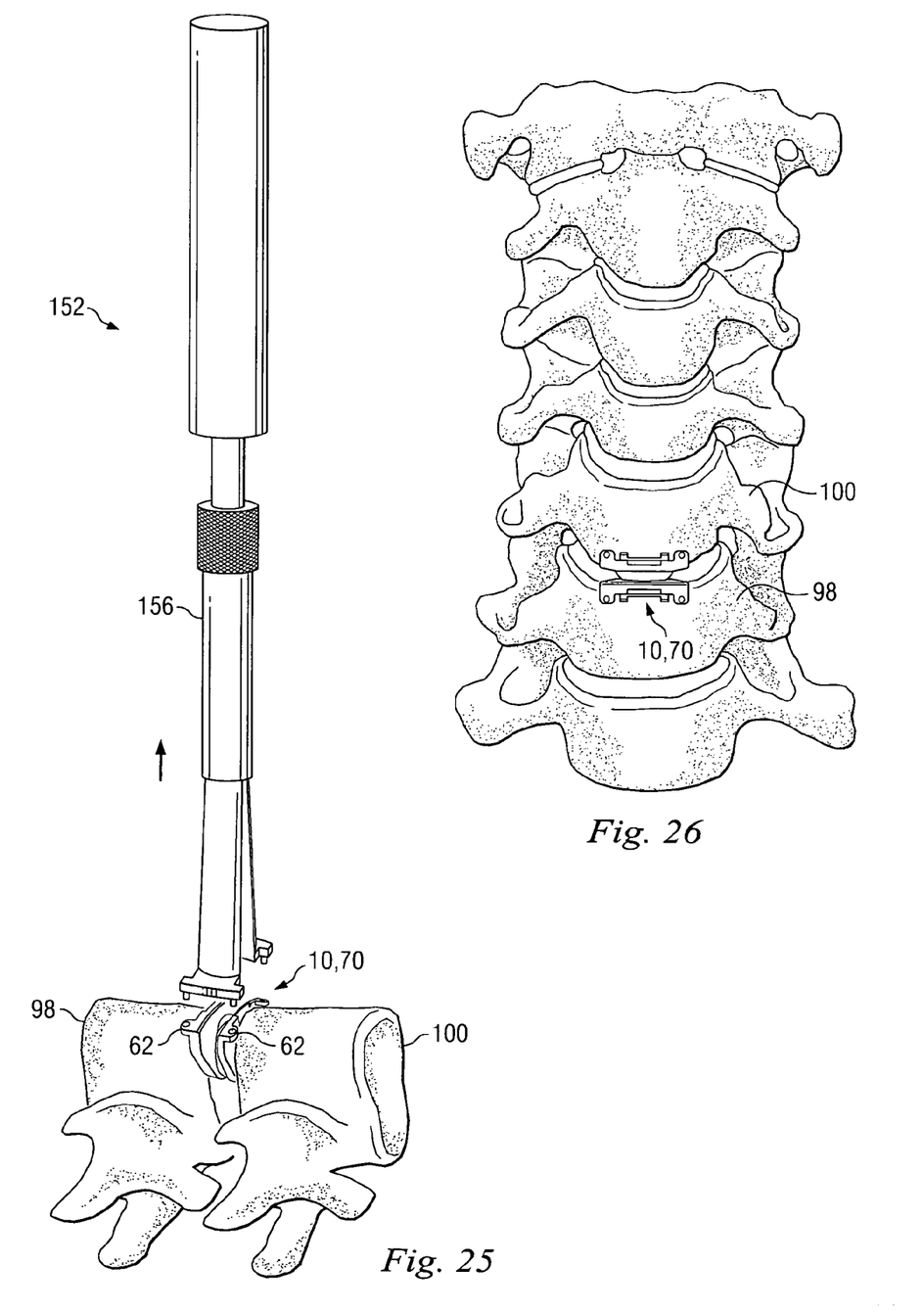
FIG. 25 is a perspective view of a representation of a method of removing the implant inserter from the implanted artificial spinal disc system of FIG. 24.
FIG. 26 is a front or anterior view of a portion of a spine that includes an artificial spinal disc implanted in the disc space of FIG. 22.

Referring back to FIG. 17, to position the rail cutter guide 118 relative to the adjacent vertebral bodies 98, 100, urging mechanism 138 may be utilized to move the rail cutter guide 118 into a desired position. For instance, in one embodiment, rail cutter guide 118 is impacted until all limiting structures 142 touch the anterior surface of the adjacent vertebrae 98, 100. Referring to FIG. 19-22, after removing urging mechanism 138, a bone removal mechanism 144 may be movable relative to machining guide 120 to create fin or rail member channel 128 (FIG. 22). In one embodiment, for example, bone removal mechanism 144 may include a drill bit 146 attachable to either an actuation mechanism 148, such as a power source or a manual drill bit handle. In this embodiment, drill bit 146 is inserted into one port formed within machining guide 120 on rail cutter guide 118, and operates to form one channel 128 in the endplate. Referring specifically to FIG. 21, it may be desired to secure the relative position of rail cutter guide 118 and the first-formed channel 128 (not shown) in order to insure proper geometric alignment of successive channels. In such a situation, a temporary fixation mechanism 150, such as a pin or screw, may be secured to rail cutter guide 118, such as to machining guide 120. Then, the successive channels 128 may be formed, and additional temporary fixation mechanisms 150 may be applied. Referring specifically to FIG. 22, after removing any temporary fixation mechanisms 150 and rail cutter guide 118, one or both endplates should have one or more properly positioned channels 128.

Referring to FIGS. 23-26, an artificial spinal disc system 10 or 70, such as the PRESTIGE Cervical Disc manufactured by Medtronic Sofamor Danek USA (Memphis, Tenn.) may be attached onto an implant inserter 152. In one embodiment, for example, the implant inserter 152 includes four inserter prongs 154 (only 3 are visible in FIG. 23), attached to legs 155 positioned within outer sheath 156, that fit into holes 64 within tabs 62. Outer sheath 156 is advanced to apply a force across the prongs 154 to hold the disc system 10 or 70. The one or more fin or rail members 54 are aligned with one or more channels 28 on the endplates of the adjacent vertebrae 98, 100, and the disc system 10 or 70 is inserted into the prepared disc space 114. Insertion may be aided by urging mechanism 138, and disc system 10 or 70 is advanced until the anteriorly positioned tabs 62 come into contact with the anterior surface of the adjacent vertebral bodies 98, 100. Disc system 10 or 70 may then be released by implant inserter 152, for example by sliding back outer sheath 156 and gently removing implant inserter 152. Final placement of disc system 10 or 70 between adjacent vertebrae 98, 100 may be verified using medical diagnostic equipment, such as by using fluoroscopy. The surgery may be completed using standard closure procedures.

Thus, the present invention includes various embodiments of artificial spinal discs having predetermined bone in-growth areas and additional features to aid in the removal or revision of the implanted artificial disc. Additionally, the present invention includes various embodiments of fin or guide rail channel-forming mechanisms, and of methods of implanting artificial discs having at least one fin or guide rail member.

The present disclosure describes several artificial spinal disc systems with relatively-symmetrical members 12 and 14. It will nevertheless be understood that in some embodiments, the members 12 and 14 may be asymmetrical. For example, in one embodiment, both of the growth area indicators 32 and 34 can be similarly configured as, for example, an indentation. In another embodiment, the growth indicator 32 may be an indentation and the growth indicator 34 may be a projection. In still other embodiments, only one growth indicator may be used. For example, surface 16 may have growth area indicator 32 while surface 18 has no growth area indicator. It is therefore understood that there is a wide range of embodiments herein disclosed, with different combinations of different elements.

While the various embodiments of the present invention have been illustrated and described, it will be clear that the present invention is not limited to these embodiments only. For instance, all or predetermined portions of the bone-contacting surfaces of the artificial disc systems may comprise bone in-growth surfaces. Numerous modifications, changes, variations, substitutions and equivalents will be apparent to those skilled in the art without departing from the spirit and scope of the present invention as described in the claims.

What is claimed is:

1. An intervertebral disc prosthesis for insertion between a superior vertebra and an inferior vertebra, the intervertebral disc prosthesis comprising:
   a superior component for engaging the superior vertebra, the superior component comprising:
      a superior surface for contacting an endplate of the superior vertebra;
      a pair of superior rails extending from the superior surface substantially parallel to each other;
      a superior bone in-growth area located on the superior surface between the pair of rails; and
      a superior bone in-growth indicator comprising a sloped surface extending from an edge of the superior surface towards the superior bone in-growth area; and
   an inferior component for articulating with the superior component and for engaging the inferior vertebra, the inferior component comprising:
      an inferior surface for contacting an endplate of the inferior vertebra;
      a pair of inferior rails extending from the inferior surface substantially parallel to each other;
      an inferior bone in-growth area located on the inferior surface between the pair of rails; and
      an inferior bone in-growth indicator comprising a sloped surface extending from an edge of the inferior surface towards the inferior bone in-growth area;
   wherein the edge of the superior surface extends beyond the endplate of the superior vertebra when the prosthesis is inserted between the superior and inferior vertebrae.

2. The prosthesis of claim 1 wherein the edge of the superior surface extends beyond the endplate of the superior vertebra when the prosthesis is inserted between the superior and inferior vertebrae.

3. An intervertebral disc prosthesis for insertion between a superior vertebra and an inferior vertebra, the intervertebral disc prosthesis comprising:
a superior component for engaging the superior vertebra, the superior component comprising:
a superior surface for contacting an endplate of the superior vertebra;
a pair of superior rails extending from the superior surface substantially parallel to each other;
a superior bone in-growth area located on the superior surface between the pair of rails; and
a superior bone in-growth indicator comprising a sloped surface extending from an edge of the superior surface towards the superior bone in-growth area;
at least one superior tab extending from the edge of the superior surface of the superior component for preventing migration of the prosthesis after insertion; and
an inferior component for articulating with the superior component and for engaging the inferior vertebra, the inferior component comprising:
an inferior surface for contacting an endplate of the inferior vertebra;
a pair of inferior rails extending from the inferior surface substantially parallel to each other;
an inferior bone in-growth area located on the inferior surface between the pair of rails; and
an inferior bone in-growth indicator comprising a sloped surface extending from an edge of the inferior surface towards the inferior bone in-growth area.

4. The prosthesis of claim 3 wherein the at least one superior tab is not affixed to either the superior or inferior vertebrae.

5. The prosthesis of claim 3 further comprising at least one inferior tab extending from the edge of the inferior surface of the inferior component for preventing migration of the prosthesis after insertion.

6. An intervertebral device comprising:
an endplate assembly comprising
an engagement surface for contacting a vertebra;
a pair of rails extending from the engagement surface;
a bone in-growth area located on the engagement surface between the pair of rails;
a non in-growth area located on the engagement surface between the edges of the engagement surface and the pair of rails;
a revision guide having a sloped surface extending from an edge of the engagement surface across at least a portion of the non in-growth area towards the bone in-growth area, the revision guide adapted for guiding a revision tool to the bone in-growth area during a revision surgery; and
a bone in-growth indicator positioned adjacent the revision guide for identifying the location of the bone in-growth area.

7. The prosthesis of claim 6 wherein the bone in-growth area is positioned at least partially above the engagement surface.

8. The prosthesis of claim 7 wherein the bone in-growth area is disposed centrally on the engagement surface.

9. The prosthesis of claim 6 wherein the bone in-growth indicator is an indention.

10. The prosthesis of claim 6 wherein the bone in-growth indicator is a projection.

11. The prosthesis of claim 6 wherein the bone in-growth indicator is an embedded marker.

12. The prosthesis of claim 6 wherein the bone in-growth indicator is visible by the naked eye.

13. The prosthesis of claim 6 wherein the bone in-growth indicator is visible with medical diagnostic equipment.

14. An intervertebral disc prosthesis comprising:
an endplate assembly comprising an engagement surface for contacting an endplate of a vertebra;
a pair of elongated protrusions extending from the engagement surface, the pair of elongated protrusions adapted to engage the endplate of the vertebra;
a bone in-growth area located on the engagement surface between the edges of the engagement surface and the pair of elongated protrusions;
a non in-growth area located on the engagement surface substantially outside of the pair of elongated protrusions; and
a bone in-growth indicator comprising a sloped surface extending from an edge of the engagement surface towards the bone in-growth area.

15. The intervertebral disc prosthesis of claim 14, wherein the bone in-growth indicator is adapted for guiding a revision tool to the bone in-growth area for separating the bone in-growth area from the endplate of the vertebra.

16. The intervertebral disc prosthesis of claim 15, wherein at least a portion of the sloped surface of the bone growth indicator extends beyond an outer boundary of the endplate of the vertebra when the engagement surface contacts the endplate.

17. The intervertebral disc prosthesis of claim 15, wherein the bone in-growth area is positioned centrally on the engagement surface.

18. The intervertebral disc prosthesis of claim 17, wherein the sloped surface of the bone growth indicator extends across a portion of the non in-growth area.

* * * * *